United States Patent
Giuliani et al.

(10) Patent No.: US 9,241,888 B2
(45) Date of Patent: Jan. 26, 2016

(54) PHARMACEUTICAL OR COSMETIC COMPOSITION FOR TREATING ALOPECIA

(71) Applicant: GIULIANI S.P.A., Milan (IT)

(72) Inventors: Giammaria Giuliani, Milan (IT); Ralf Paus, Hamburg (DE); Anna Benedusi, Milan (IT); Barbara Marzani, Carbonara al Ticino (IT); Sergio Baroni, Villa d'adda (IT)

(73) Assignee: Giuliani S.P.A., Milan (IT)

( * ) Notice: Subject to any disclaimer, the term of this patent is extended or adjusted under 35 U.S.C. 154(b) by 0 days.

(21) Appl. No.: 14/417,598

(22) PCT Filed: Jul. 26, 2013

(86) PCT No.: PCT/EP2013/065793
§ 371 (c)(1),
(2) Date: Jan. 27, 2015

(87) PCT Pub. No.: WO2014/016407
PCT Pub. Date: Jan. 30, 2014

(65) Prior Publication Data
US 2015/0202132 A1    Jul. 23, 2015

(30) Foreign Application Priority Data
Jul. 27, 2012  (IT) .............................. MI2012A1323

(51) Int. Cl.
| | | |
|---|---|---|
| *A01N 33/02* | (2006.01) | |
| *C07C 211/00* | (2006.01) | |
| *A61K 8/41* | (2006.01) | |
| *A61Q 7/00* | (2006.01) | |
| *A61K 31/132* | (2006.01) | |
| *C07C 211/14* | (2006.01) | |

(52) U.S. Cl.
CPC ................. *A61K 8/41* (2013.01); *A61K 31/132* (2013.01); *A61Q 7/00* (2013.01); *C07C 211/14* (2013.01)

(58) Field of Classification Search
CPC ..................................................... A61K 31/132
USPC ......................................... 514/674; 564/512
See application file for complete search history.

(56) References Cited

FOREIGN PATENT DOCUMENTS

| | | |
|---|---|---|
| EP | 1469843 A1 | 10/2004 |
| WO | 9937277 A1 | 7/1999 |
| WO | 02062341 A1 | 8/2002 |

OTHER PUBLICATIONS

International Search Report and Written Opinion for corresponding application No. PCT/EP2013/065793 mailed Dec. 3, 2013.

*Primary Examiner* — Nizal Chandrakumar
(74) *Attorney, Agent, or Firm* — LeClairRyan, a Professional Corporation

(57) ABSTRACT

The present invention relates to a cosmetic or pharmaceutical composition for treating alopecia, and in general for counteracting excessive hair loss, comprising as an active ingredient a compound of formula (I) R—$N^1$-spermidine, or 1,4-butanediamine,N-(3-aminopropyl)-$N^1$—R. The compounds of general formula (I) are active in accordance with the objects of the present invention, and also sufficiently stable to allow effective application for topical use on the scalp without potentially being transformed into a different substance, which is no longer active, as a result of oxidation.

10 Claims, 9 Drawing Sheets

PHARMACEUTICAL OR COSMETIC COMPOSITION FOR TREATING ALOPECIA

This application is a national stage application under 35 U.S.C. §371 of PCT Application No. PCT/EP2013/065793, filed 26 Jul. 2013, which claims the priority benefit of Italy Application No. MI2012A001323, filed 27 Jul. 2012, which are hereby incorporated by reference in their entirety.

FIELD OF THE INVENTION

The present invention relates to a pharmaceutical or cosmetic composition for treating alopecia and in general for combating excessive hair loss.

PRIOR ART

The hair follicle (HF) is one of the most complex mini-organs in the human body with the capacity to regenerate. The growth cycle of hair during post-natal life describes the morphohistological changes to the shaft and the follicle over time. The cyclic activity starts with the production of hair, followed by a rapid growth and elongation of the shaft (anagen phase). The follicle and the hair subsequently undergo a regression driven by apoptosis (catagen phase), followed by a rest phase (telogen) and finally a hair loss phase (exogen).

These transformations involve a rapid remodeling of epithelial and dermal components based on changes in the expression and/or activity of cytokines, hormones, enzymes, neurotransmitters and their cognate receptors, and transcription factors that are recognised as key mediators of the hair cycle.

All of the hairs of the body are subject to a similar life cycle, although the extension, the duration of the phases and the length of the shaft vary between different areas of the body and between individuals depending on their genetic programming, age and state of health. Moreover, many regulators are involved in the biology of hair, affecting morphogenesis and regulating the initiation of the anagen phase and the duration.

There are various hormones involved in regulating hair growth cycle, including melatonin, prolactin, the melanocyte-stimulating hormone (MSH), thyroid hormone and estrogens. For example, it has been found that prolactin is involved in the regulation of hair growth in both mice and humans.

Many of these regulators may be a target of clinical treatments. For example, excluding pubic and armpit follicles, androgens require the enzyme 5α-reductase, which is capable of metabolising testosterone to 5α-dihydrotestosterone (DHT), the more potent metabolite. This is in fact a mechanism used in both the clinical and the cosmetic field to counteract hair loss in cases of androgenetic alopecia.

As opposed to hair loss, excessive growth of hair can be a problem, particularly for women. By contrast with androgenetic alopecia, hirsutism and hypertrichosis result from an extended anagen phase accompanied by an abnormal enlargement of hair follicles.

The usual treatments to combat this state are the use of depilatory creams and waxes, which only relieve the problem temporarily since the irritation or tearing rapidly induces the anagen phase of the hair follicle and regrowth. Other systems used are electrolysis and selective photothermolysis, with the use of lasers to destroy the hair shaft and the dermal papilla of the hair follicles. The latest treatments available are very aggressive.

To solve these problems, new and more effective methods are needed. In recent decades, there is particular scientific interest in the role of ornithine decarboxylase (ODC) and polyamines in the hair cycle. This interest is primarily due to the fact that the follicle is one of the most highly proliferative organs. ODC, the rate-limiting enzyme in polyamine biosynthesis, is a target for inhibitor drugs (such as eflornithine), which results in a decrease in the speed of facial hair growth in vivo and inhibition of the growth of human hair in organ culture.

For clinical purposes, for controlling the amount of hair produced, one strategy is to change the duration of anagen, shortening it in cases of hirsutism or increasing it to combat alopecia. In general, disorders of the human follicle such as hirsutism, grey hair and alopecia have considerable negative effects on the psyche and self-esteem of the individuals affected.

Patent EP 1469843 by the same applicant discloses a composition for pharmaceutical, cosmetic or dietetic use for combating hair loss, in which the active ingredient is the polyamine known as spermidine, or N'-(3-aminopropyl)-1,4-diaminobutane, both for oral use and for topical use on the scalp. The formula for spermidine is: $H_2N-(CH_2)_3-NH-(CH_2)_4-NH_2$.

This patent reports experimental evidence that a composition containing spermidine, both as such and in combination with other micronutrient additives, can slow and stop excessive hair loss, and at the same time improve the resistance and the general state of health of the hair. The tensile test showed that spermidine increases the tensile strength of the hair, whilst the trichogram and wash-test showed the improvements that occur in the hair bulb. In addition to a substantial decrease in the number of hairs lost after washing, the number of hairs lost in telogen phase (pathological loss) is also reduced with respect to the number of hairs lost in the exogen phase (loss for natural replacement). Treatment with spermidine thus substantially improves the hair cycle altered by the disease of hair loss in telogen, bringing it back to normal physiological levels. Spermidine is therefore an effective active ingredient for combating alopecia.

However, spermidine, like other polyamines, is subject to oxidation, especially in the case of topical application on the scalp, in which the compound remains in extended contact with the air for some time before being absorbed by the skin and performing its action. Any oxidation of spermidine during this time before the absorption would lead to oxidation products which are no longer active, if not potentially harmful.

The present invention primarily aims to find a solution to this problem. Of the theoretical solutions, potential chemical protection of the amine functional groups subject to oxidation does not appear to be generally suitable in practice, especially in view of the prior art summarised by the following patents.

WO9937277 describes substituted polyamines for reducing the growth of the hair of mammals by selecting of an area of skin where this effect is to be produced and applying to this area of skin a dermatologically acceptable composition, comprising a substituted polyamine as an inhibitor for the biosynthetic hypusine pathway, in an amount which effectively reduces the growth of hair. Unwanted hair growth in mammals, including humans, particularly hair growth stimulated by androgens, can thus be reduced either in cases of normal growth, or equally in cases of an increase resulting from abnormalities or disorders (for example hirsutism).

WO02062341 relates to a pharmaceutical composition suitable for topical application on a human or non-human mammal for controlling the growth of hair in the area in which it is applied, comprising an effective amount of a substituted polyamine or a salt thereof. An ODC (ornithine decarboxylase) inhibition mechanism from polyamine, which binds irreversibly with the ODC present in the cell so as to prevent ODC from catalysing the decarboxylation of ornithine to putrescine, is described in this case. According to this patent, hair growth can be regulated by applying particular substituted polyamines, which primarily prevent the formation of ODC in the cells into which they are absorbed, to human and non-human mammals. In this way, rather than acting as true ODC inhibitors, it is believed that the substituted polyamines in question work by preventing the synthesis of ODC. The experimental examples in this document show that the administered polyamine, in this case diethylhomospermine, halts the regrowth of shaved hair in mice.

SUMMARY OF THE INVENTION

In any case, irrespective of the biological mechanism behind the final achieved effect of preventing hair growth, this known prior art clearly does not encourage, as a hypothetical practical solution, the solution of substituting the spermidine with functional groups so as to obtain an opposite effect of stimulating growth in the area of application on the skin of the scalp, which is the object of the present invention.

At the same time, a further object of the present invention is to provide compounds which may be, at least for some properties, even more active than spermidine in combating hair loss.

DETAILED DESCRIPTION OF THE INVENTION

Contrary to what might be supposed from the prior art summarised above, according to the present invention, it has now surprisingly been found that the following compounds of formula (I) R—$N^1$-spermidine, or 1,4-butanediamine,N-(3-aminopropyl)-$N^1$—R, $$H_2N—(CH_2)_3—N^1(R)—(CH_2)_4—NH_2 \quad (I)$$

wherein R is a substituent bound to the secondary amine function of spermidine, chosen from:
- saturated or unsaturated, linear or branched alkyl groups, consisting of 1 to 6 carbon atoms, in which optionally one or more carbon atoms are substituted by fluorine, such as methyl, ethyl, trifluoromethyl, trifluoroethyl, propyl, isopropyl, butyl, isobutyl, pentyl, hexyl, ethylene, vinyl, propylene, butylene;
- aryl or arylalkyl groups such as phenyl, naphthyl, benzyl, tolyl, wherein optionally one or more carbon atoms are substituted by fluorine, and wherein said arylalkyl groups comprise saturated or unsaturated, linear or branched alkyl groups, consisting of 1 to 6 carbon atoms, wherein optionally one or more carbon atoms are substituted by fluorine, such as methyl, ethyl, trifluoromethyl, trifluoroethyl, propyl, isopropyl, butyl, isobutyl, pentyl, hexyl, ethylene, vinyl, propylene, butylene;
- saturated or unsaturated cycloalkyl groups consisting of 3 to 8 carbon atoms, optionally substituted with saturated or unsaturated, linear or branched alkyl groups, consisting of 1 to 6 carbon atoms, wherein optionally one or more carbon atoms are substituted by fluorine, such as methyl, ethyl, trifluoromethyl, trifluoroethyl, propyl, isopropyl, butyl, isobutyl, pentyl, hexyl, ethylene, vinyl, propylene, butylene;
- or a pharmaceutically acceptable salt thereof, have an anti-hair loss activity substantially comparable with spermidine, but without being subject to the problem of oxidation in the presence of ambient air during topical application to the scalp. In fact, they are so stable with respect to air that they make effective application possible for topical use on the scalp without being transformed into oxidised by-products which are inactive, or not active in accordance with the objects of the present invention.

In particular, also surprisingly, these compounds according to the present invention turn out to be more active than spermidine in combating alopecia, at least with respect to particular properties as described above.

The present invention therefore relates to the use of these R—$N^1$-spermidine compounds (I) to combat hair loss and to compositions for pharmaceutical or cosmetic use which comprise them as active ingredients.

A preferred compound of formula (I) according to the present invention is $N^1$-methylspermidine, or N-(3-aminopropyl)-N'-methyl-1,4-butanediamine (CAS Registry Number 51460-23-2), of formula:

$$H_2N—(CH_2)_3—N^1(CH_3)—(CH_2)_4—NH_2 \quad (II)$$

used in a composition according to the invention as such or as a pharmaceutically acceptable salt, for example trihydrochloride (3HCl) or trimaleate. A further preferred compound of formula (I) according to the present invention is $N^1$-cyclohexylspermidine, or N-(3-aminopropyl)-$N^1$-cyclohexyl-1,4-butanediamine (CAS Registry Number 183070-28-2), of formula:

$$H_2N—(CH_2)_3—N^1(C_6H_{11})—(CH_2)_4—NH_2 \quad (III)$$

used in a composition according to the invention as such or as a pharmaceutically acceptable salt, for example trihydrochloride (3HCl) or trimaleate. A further preferred compound of formula (I) according to the present invention is $N^1$-ethylspermidine, or N-(3-aminopropyl)-$N^1$-ethyl-1,4-butanediamine (CAS Registry Number 97141-36-1), of formula:

$$H_2N—(CH_2)_3—N^1(C_2H_5)—(CH_2)_4—NH_2 \quad (IV)$$

used in a composition according to the invention as such or as a pharmaceutically acceptable salt, for example trihydrochloride (3HCl) or trimaleate. A further preferred compound of formula (I) according to the present invention is $N^1$-propylspermidine, or N-(3-aminopropyl)-$N^1$-propyl-1,4-butanediamine (CAS Registry Number 62659-14-7), of formula:

$$H_2N—(CH_2)_3—N^1(C_3H_7)—(CH_2)_4—NH_2 \quad (V)$$

used in a composition according to the invention as such or as a pharmaceutically acceptable salt, for example trihydrochloride (3HCl) or trimaleate. A further preferred compound of formula (I) according to the present invention is $N^1$-isobutylspermidine, or N-(3-aminopropyl)-$N^1$-isobutyl-1,4-butanediamine, of formula:

$$H_2N—(CH_2)_3—N^1(C_4H_9)—(CH_2)_4—NH_2 \quad (VI)$$

used in a composition according to the invention as such or as a pharmaceutically acceptable salt, for example trihydrochloride (3HCl) or trimaleate. This compound (VI) is not known in the literature. A method for synthesising it is therefore described in the following, referring to the following reaction scheme in which compound (VI) is separated out as compound 4.

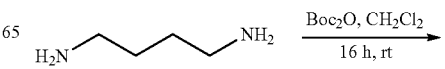

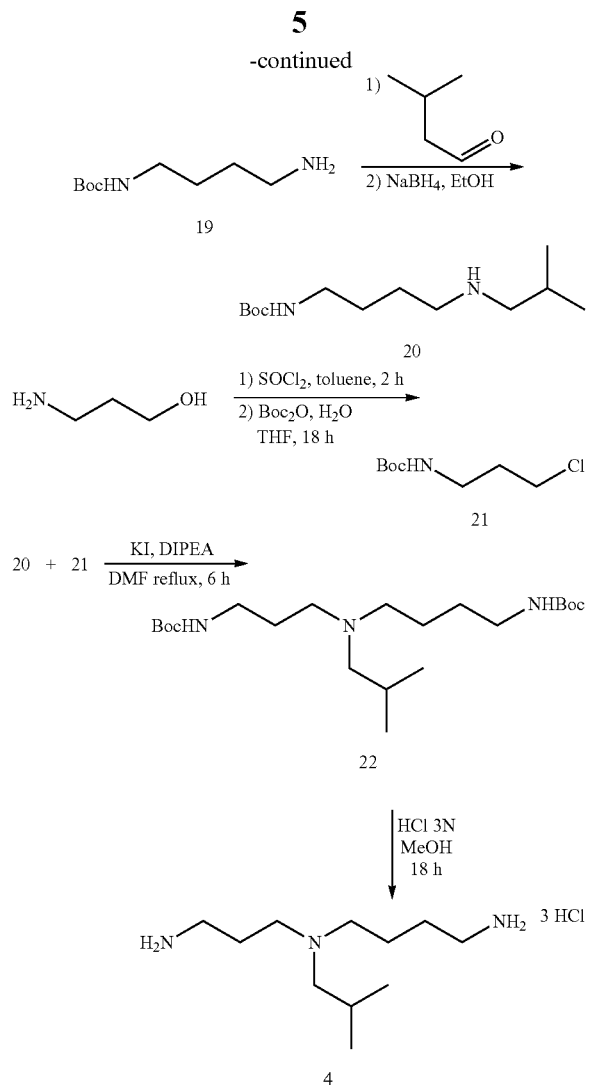

Synthesis of compound 19: butane diamine (1 g, 0.0113 mol, 5 eq) was solubilised in CH$_2$Cl$_2$ (15 ml). To the solution was added Boc$_2$O (0.619 g, 0.00283 mol, 1 eq) solubilised in CH$_2$Cl$_2$ (15 ml). The reaction mixture was left to stir at RT for 16 hours. The structure of the product was evaluated by TLC CH$_2$Cl$_2$ 8/MeOH 2/NH$_4$Oaq 33% 0.2. The suspension formed was filtered and the filtrate was dried by rotary evaporator. The oily residue was eluted with EtOAc (15 ml) and washed with a saturated NaCl solution (3×10 ml) to remove the excess unreacted diamine. The organic extracts were dehydrated over sodium sulphate and evaporated. 0.520 g of a yellow oil were obtained. Yield 97.65%. $^1$H NMR (400 MHz, CDCl$_3$) δ 1.38 (s, 9H), 1.52-1.59 (m, 4H), 2.34 (brs, 2H, D$_2$O exch.), 2.72-2.79 (m, 2H), 3.19-3.24 (m, 2H), 5.95 (brs, 1H, D$_2$O exch.).

Synthesis of compound 20: the aforementioned compound 19 (0.358 g, 0.00190 mol, 1 eq) was solubilised in EtOH (5 ml). To the solution were added 3 A molecular sieves and isobutyraldehyde (0.137 g, 0.00190 mol, 0.17 ml, 1 eq). The reaction mixture was stirred at RT for 18 hours. NaBH$_4$ (0.144 g, 0.0038 mol, 2 eq) was added and the mixture was stirred at RT for 16 h. The structure of the product was evaluated by TLC CH$_2$Cl$_2$ 9/MeOH 1/NH$_4$OHaq 33% 0.1. The solvent was evaporated, and the oily residue was eluted with CH$_2$Cl$_2$ (10 ml) and washed with saturated NaCl solution (5 ml). The organic extracts were dehydrated over sodium sulphate and evaporated, and the residue obtained was purified by flash chromatography using a mixture of CH$_2$Cl$_2$ 9/MeOH 1/NH$_4$OHaq 33% 0.1 as the eluent phase. 0.215 mg of a colourless oil were obtained. Yield 46.33%. $^1$H NMR (400 MHz, CDCl$_3$) δ 0.88 (d, 6H, J=6.8 Hz), 1.41 (s, 9H), 1.49-1.52 (m, 4H), 1.72-1.75 (m, 1H), 2.38 (d, 2H, J=7.2 Hz), 2.59 (t, 2H, J=6.6 Hz), 3.07-3.09 (m, 2H), 4.95 (brs, 1H, D$_2$O exch.).

Synthesis of compound 21: aminopropanol (0.49 g, 0.51 ml, 0.00652 mol, 1 eq) was solubilised in toluene (5 ml). To the solution was added SOCl$_2$ (3.10 g, 1.90 ml, 0.00261 mol, 4 eq) in an ice bath. The reaction mixture was stirred under reflux for 2 hours. The structure of the product was evaluated by TLC CH$_2$Cl$_2$ 9/MeOH 1/NH$_4$OHaq 33% 0.1. The solvent was evaporated, and the oily residue was eluted with H$_2$O (10 ml) and washed with CH$_2$Cl$_2$ (5 ml). The aqueous phase was used without further purifications in the following step, Net3 (0.659 mg, 0.9 ml, 0.00652 mol, 1 eq) was added to the solution, and the mixture was stirred at RT for 30 minutes. A solution of Boc$_2$O (1.42 g, 0.00652 mol, 1 eq) in THF (10 ml) was added. The reaction mixture was stirred at RT for 18 hours. The disappearance of the starting product was evaluated by TLC petroleum ether 8/EtOAc 2. The solvents were evaporated, and the residue was eluted with EtOAc and washed with H$_2$O. The organic extracts were dehydrated over sodium sulphate and evaporated. 1.23 g of a brown oil were obtained. Yield 97.70%. $^1$H NMR (400 MHz, CDCl$_3$) δ 1.43 (s, 9H), 1.94-1.97 (m, 2H), 3.26 (t, 2H, J=6.4 Hz), 3.58 (t, 2H, J=6.4), 4.75 (brs, 1H, D$_2$O exch.).

Synthesis of compound 22: the aforementioned compound 20 (0.120 g, 0.00049 mol, 1 eq) was solubilised in DMF (3 ml). To the solution was added the aforementioned compound 21 (0.104 g, 0.00054 mol, 1.1 eq) solubilised in DMF (2 ml). The reaction mixture was stirred under reflux for 6 hours. The structure of the product was evaluated by TLC CH$_2$Cl$_2$ 9/MeOH 1/NH$_4$OHaq 33% 0.03. The solvent was evaporated, and the oily residue was purified by flash chromatography using a mixture of CH$_2$Cl$_2$ 9/MeOH 1/NH$_4$OHaq 33% 0.03 as the eluent phase. 0.084 mg of a yellow oil were obtained. Yield 42.71%. $^1$H NMR (400 MHz, CDCl$_3$) δ 0.87 (d, 6H, J=6.8 Hz), 1.43 (s, 18H), 1.57-1.61 (m, 7H), 1.98-2.01 (m, 2H), 2.31-2.35 (m, 2H), 2.38-2.42 (m, 2H), 3.10-3.12 (m, 2H), 3.16-3.18 (m, 2H), 4.72 (brs, 1H, exch D$_2$O), 5.69 (brs, 1H, D$_2$O exch.).

Synthesis of compound 4: onto said compound 22 (0.084 g, 0.00021 mol, 1 eq), solubilised in MeOH (2 ml) and kept in an ice bath, was dripped HCl 3N (10 ml). The reaction mixture was stirred at room temperature for 18 hours. The disappearance of the starting product was evaluated by TLC (CH$_2$Cl$_2$ 9/MeOH 1/NH$_4$OHaq 0.03). The MeOH was evaporated, and the aqueous residue was washed with ethyl ether (2×8 ml) and dried. 0.065 g of compound 4 were obtained as a trihydrochloride salt. Yield 100%. $^1$H NMR (400 MHz, D$_2$O) δ 1.02 (d, 6H, J=6.8 Hz), 1.76-1.78 (m, 2H), 1.79-1.84 (m, 2H), 2.14-2.17 (m, 3H), 3.06-3.25 (m, 6H), 3.26-3.33 (m, 4H); $^{13}$C NMR (100 MHz, D$_2$O) δ 19.27, 20.15, 21.26, 23.83, 28.92, 36.52, 38.77, 50.18, 52.66, 58.88, 60.59. MS (ESI+) m/z=202 (M+H)+

FIGS. 7, 8 and 9 of the appended drawings show, respectively, $^1$H-NMR, $^{13}$C-NMR and mass spectra of compound 4, that is, of formula (VI) as defined above.

Example Compositions

In the following, some examples of compositions according to the invention for topical use on the scalp are described by way of non-limiting example. In the following examples, the $N^1$-methyl spermidine is referred to by the corresponding INCI name required for use in cosmetic products, namely: N-methylspermidine. This also applies to the other inventive compounds given as examples.

Example 1

Shampoo Treatment for Reducing Hair Loss

| Component (INCI name) | Amount % p/p |
|---|---|
| Disodium Laureth Sulfosuccinate | 1.00-5.00 |
| Magnesium Laureth Sulfate | 5.00-9.00 |
| PEG-7 Glyceryl Cocoate | 0.50-1.00 |
| Cocamide MIPA | 0.50-2.00 |
| Peg-200 Hydrogenated Glyceryl Palmate | 0.50-2.00 |
| Polyquaternium-10 | 0.10-0.50 |
| Sodium Lauroyl Sarcosinate | 1.00-4.00 |
| Tetrasodium EDTA | 0.05-0.20 |
| N-methylspermidine | 0.001-0.30 |
| Biotin | 0.01-0.10 |
| Calcium pantothenate | 0.01-3.0 |
| Potassium Undecylenoyl Wheat Protein | 0.50-1.00 |
| Laureth-4 | 0.01-0.80 |
| Parfum | 0.10-0.80 |
| Glycol Distearate | 0.50-1.00 |
| Laureth-7 | 0.50-0.80 |
| Sodium Cocoamphoacetate | 0.05-3.00 |
| Cocamidopropyl Betaine | 0.01-2.00 |
| Sodium Laureth Sulfate | 0.01-3.00 |
| Sodium Hydroxymethylglycinate | 0.20-0.45 |
| Sodium hydroxide | q.s. |
| Citric acid | q.s. |
| Aqua | q.s. 100.00 |

Example 2

Lotion Treatment for Reducing Hair Loss

| Component (INCI name) | Amount % p/v |
|---|---|
| Aqua | q.s. 100 ml |
| Hydroxypropyltrimonium Hyaluronate | 0.005-0.50 |
| Polyurethane-26 | 0.004-4.0 |
| Lecithin (*Glycine max* L.) | 0.005-5.0 |
| Denatured alcohol | 15.0-20.0 |
| N-methylspermidine | 0.005-0.30 |
| Biotin | 0.01-0.10 |
| Calcium pantothenate | 0.1-3.0 |
| Rutin | 0.001-0.05 |
| PEG-40 Hydrogenated Castor Oil | 0.5-2.0 |
| Octadecyl Di-t-butyl-4-hydroxyhydrocinnamate | 0.05 |
| Parfum | 0.20 |
| Zeaxanthin | 0.002-0.01 |
| *Helianthus annuus* seed oil | 0.001-0.01 |
| Lactic acid | q.s. for pH 5.0 |

Example 3

Balsam Conditioner Assisting in Reducing Hair Loss

| Component (INCI name) | Amount % p/v |
|---|---|
| Aqua | q.s. 100 ml |
| Cetearyl alcohol | 0.50-7.00 |
| PEG-40 hydrogenated castor oil | 0.50-2.00 |
| Stearalkonium chloride | 0.10-2.00 |
| N-methylspermidine | 0.010-0.30 |
| Disodium EDTA | 0.025-0.05 |
| Parfum | 0.20 |
| Sodium Hydroxymethylglycinate | 0.20-0.45 |
| Lactic acid | q.s. for pH 5.0 |

Example 4

Balsam Treatment for Reducing Hair Loss

| Component (INCI name) | Amount p/v (%) |
|---|---|
| Aqua | q.s. 100 ml |
| Disodium EDTA | 0.025-0.05 |
| Xilitol | 0.50-1.50 |
| Panthenol | 0.50-1.50 |
| Hydroxyethyl cellulose | 0.10-0.90 |
| Cetrimonium chloride | 0.50-5.00 |
| Bis-Isobutyl PEG/PPG-20/35/Amodimethicone Copolymer | 0.05-0.75 |
| Cetyl Ethylhexanoate | 0.05-1.00 |
| Polysorbate 80 | 0.05-4.00 |
| Butylene Glycol | 0.05-3.00 |
| Cyclopentasiloxane | 0.10-3.00 |
| C12-13 alkyl lactate | 0.50-5.00 |
| Glyecryl stearate | 1.00-5.00 |
| PEG-100 stearate | 0.50-4.00 |
| Dimethicone | 1.00-4.00 |
| Dimethiconol | 0.10-0.80 |
| Cetearyl alcohol | 1.00-5.00 |
| Phenoxyethanol | 0.30-0.90 |
| Caprylyl glycol | 0.30-0.90 |
| Zeaxanthin | 0.00005-0.00030 |
| Rutin | 0.0005-0.003 |
| N-methylspermidine | 0.00010-0.15 |
| Parfum | 0.10-0.30 |

Example 5

Intensive Serum Hair Treatment

| Component (INCI name) | Amount % p/v |
|---|---|
| Aqua | q.s. 100 ml |
| Alcohol denat. Type C | 10.00-20.00 |
| Calcium pantothenate | 0.05-2.00 |
| N-methylspermidine | 0.05-0.210 |
| Potassium octatrienoate | 0.001-0.18 |
| Biotin | 0.005-0.020 |
| *Ajuga reptans* leaf extract | 0.001-0.10 |
| *Lactobacillus* soy ferment | 0.01-0.15 |
| Panthenol | 0.10-1.00 |
| Hydroxypropyltrimonium Hyaluronate | 0.002-0.50 |
| Polyurethane-26 | 0.004-4.0 |
| Lecithin (*Glycine max* L.) | 0.005-5.0 |
| PEG-40 hydrogenated castor oil | 0.50-2.00 |
| Parfum | 0.10-0.30 |
| Hydroxypropyl guar | 0.10-0.40 |
| Ethoxydiglycol | 0.10-0.70 |
| Lactic acid | 0.05-0.50 |

Example 6

Intensive Serum Anti-Loss Treatment

| Component (INCI name) | Amount % p/v |
| --- | --- |
| Aqua | q.s. 100 ml |
| Glycerine | di1.00-8.00 |
| Ammonium acrylolyl-dimethyltaurate/vp copolymer | 0.50-5.00 |
| Cyclopentasiloxane | 1.00-8.00 |
| Phenoxyethanol | 0.30-0.90 |
| Parfum | 0.10-0.70 |
| Silicone quaternium-15 | 0.20-1.90 |
| Dimethicone | 0.10-6.00 |
| Ammonium glycyrrhizate | 0.05-0.75 |
| C11-15 pareth-5 | 0.05-1.00 |
| C11-15 pareth-9 | 0.05-1.00 |
| Disodium EDTA | 0.025-0.05 |
| N-methylspermidine | 0.025-0.210 |
| Calcium pantothenate | 0.010-0.50 |
| Ethylparaben | 0.010-0.030 |
| Methylparaben | 0.05-0.120 |
| Trideceth-5 | 0.010-0.40 |
| Trideceth-10 | 0.010-0.40 |
| Lactic acid | q.s. for pH 4.5 |

Example 7

Shampoo Treatment for Reducing Hair Loss

| Component (INCI name) | Amount % p/p |
| --- | --- |
| Disodium Laureth Sulfosuccinate | 1.00-5.00 |
| Magnesium Laureth Sulfate | 5.00-9.00 |
| PEG-7 Glyceryl Cocoate | 0.50-1.00 |
| Cocamide MIPA | 0.50-2.00 |
| Peg-200 Hydrogenated Glyceryl Palmate | 0.50-2.00 |
| Polyquaternium-10 | 0.10-0.50 |
| Sodium Lauroyl Sarcosinate | 1.00-4.00 |
| Tetrasodium EDTA | 0.05-0.20 |
| N-methylspermidine trimaleate | 0.002-0.60 |
| Biotin | 0.01-0.10 |
| Calcium pantothenate | 0.01-3.0 |
| Potassium Undecylenoyl Wheat Protein | 0.50-1.00 |
| Laureth-4 | 0.01-0.80 |
| Glycol Distearate | 0.50-1.00 |
| Sodium Hydroxymethylglycinate | 0.20-0.45 |
| Aqua | q.s. 100.00 |

Example 8

Lotion Treatment for Reducing Hair Loss

| Component (INCI name) | Amount % p/v |
| --- | --- |
| Aqua | 70-90 |
| Ethyl Alcohol | 10-20 |
| Polyoxyethylenated Hydrogenated Castor Oil | 0.5-2.5 |
| Lactic Acid soln. 80% | 0.2-0.4 |
| N-methylspermidine trimaleate | 0.05-0.3 |
| Parfum Agrumes 2807/03 | 0.05-0.3 |
| Hydroxypropyltrimonium hyaluronate | 0.01-0.1 |
| Lecithin NAT 8539 | 0.01-0.1 |
| Octadecyl di-t-butyl-4-hydroxyhydrocinnamate | 0.01-0.1 |
| Fluorolink 5032 | 0.01-0.1 |

Example 9

Strengthening Styling Gel

| Component (INCI name) | Amount % p/v |
| --- | --- |
| Aqua | 85-95 |
| Fixate PLUS Polymer | 1.5-3.5 |
| PEG-40 Hydrogenated castor oil | 1-3 |
| Parfum | 0.5-2 |
| Sorbitol | 0.5-2 |
| Sodium hydroxymethylglycinate | 0.5-2 |
| Hydroxypropyl guar | 0.2-1.2 |
| Benzophenone-4 | 0.05-1 |
| Gafquat 755N | 0.05-1 |
| Disodium EDTA dihydrate | 0.05-1 |
| Taurine | 0.025-0.1 |
| Calcium D-pantothenate | 0.01-0.05 |
| Rutin | 0.005-0.02 |
| Zeaxantine | 0.005-0.02 |
| *Ajuga Reptans* dry extract | 0.005-0.02 |
| N-methylspermidine trimaleate | 0.0015-0.006 |
| Biotin | 0.0001-0.0004 |

Example 10

Lotion Treatment for Reducing Hair Loss

| Component (INCI name) | Amount % p/v |
| --- | --- |
| Alcohol denat | 15.0-20.0 |
| N-(3-aminopropyl)-N1-isobutyl-1,4-butanediamine | 0.005-0.30 |
| Biotin | 0.01-0.10 |
| Calcium pantothenate | 0.1-3.0 |
| Rutin | 0.001-0.05 |
| PEG-40 Hydrogenated Castor Oil | 0.5-2.0 |
| Octadecyl Di-t-butyl-4-hydroxyhydrocinnamate | 0.05 |
| Zeaxanthin | 0.002-0.01 |
| Lactic acid | q.s. for pH 5.0 |
| Aqua | q.s. 100 ml |

Example 11

Intensive Serum Hair Treatment

| Component (INCI name) | Amount % p/v |
| --- | --- |
| Alcohol denat. Type C | 10-20 |
| N-(3-aminopropyl)-N1-ethyl-1,4-butanediamine | 0.05-0.2.0 |
| Hydroxypropyltrimonium Hyaluronate | 0.002-0.5 |
| Polyurethane-26 | 0.004-4.0 |
| Lecithin (*Glycine max* L.) | 0.005-5.0 |
| PEG-40 hydrogenated castor oil | 0.50-2.0 |
| Hydroxypropyl guar | 0.10-0.4 |
| Ethoxydiglycol | 0.10-0.7 |
| Lactic acid | 0.05-0.5 |
| Aqua | q.s. 100 ml |

Experimental Section and Appended Graphs

The following tests were carried out on the activity of $N^1$-methylspermidine, or N-(3-aminopropyl)-$N^1$-methyl-1,4-butanediamine, the compound of formula (II) according to the invention, either as a free base or as a salt, either trihydrochloride (3HCl) or trimaleate, by comparison with spermidine (3HCl) as a control. In FIGS. 1 and 2, the relevant test is also extended to N¹-cyclohexylspermidine, N¹-ethylspermidine, N¹-propylspermidine and N¹-isobutylspermidine, namely the compounds of formulae (III), (IV), (V), (VI) according to the invention, in the form of trihydrochloride salt (3HCl).

In this connection, drawings in accordance with the following drawings are appended to the present description.

Figure 7:
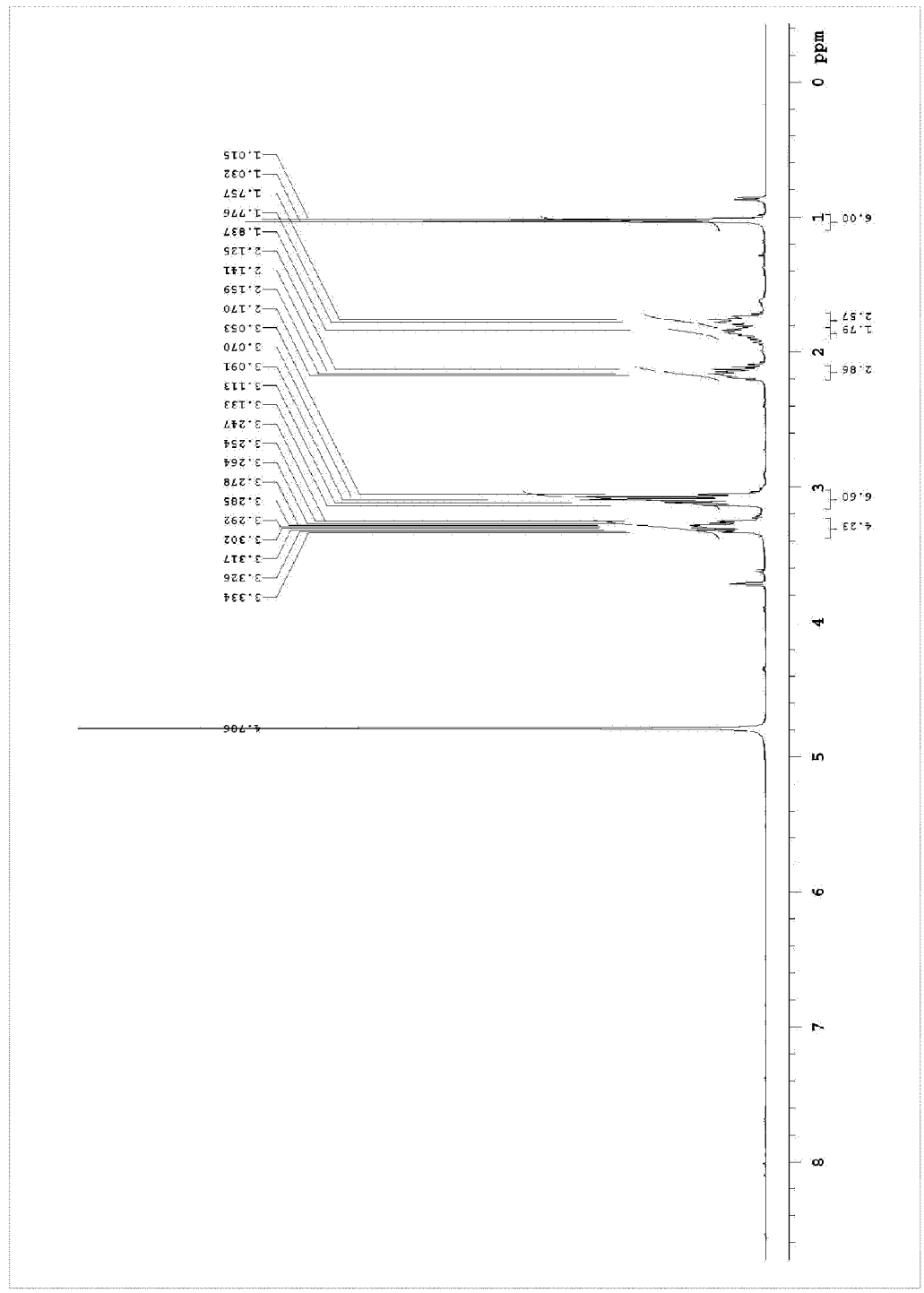
Figure 8:
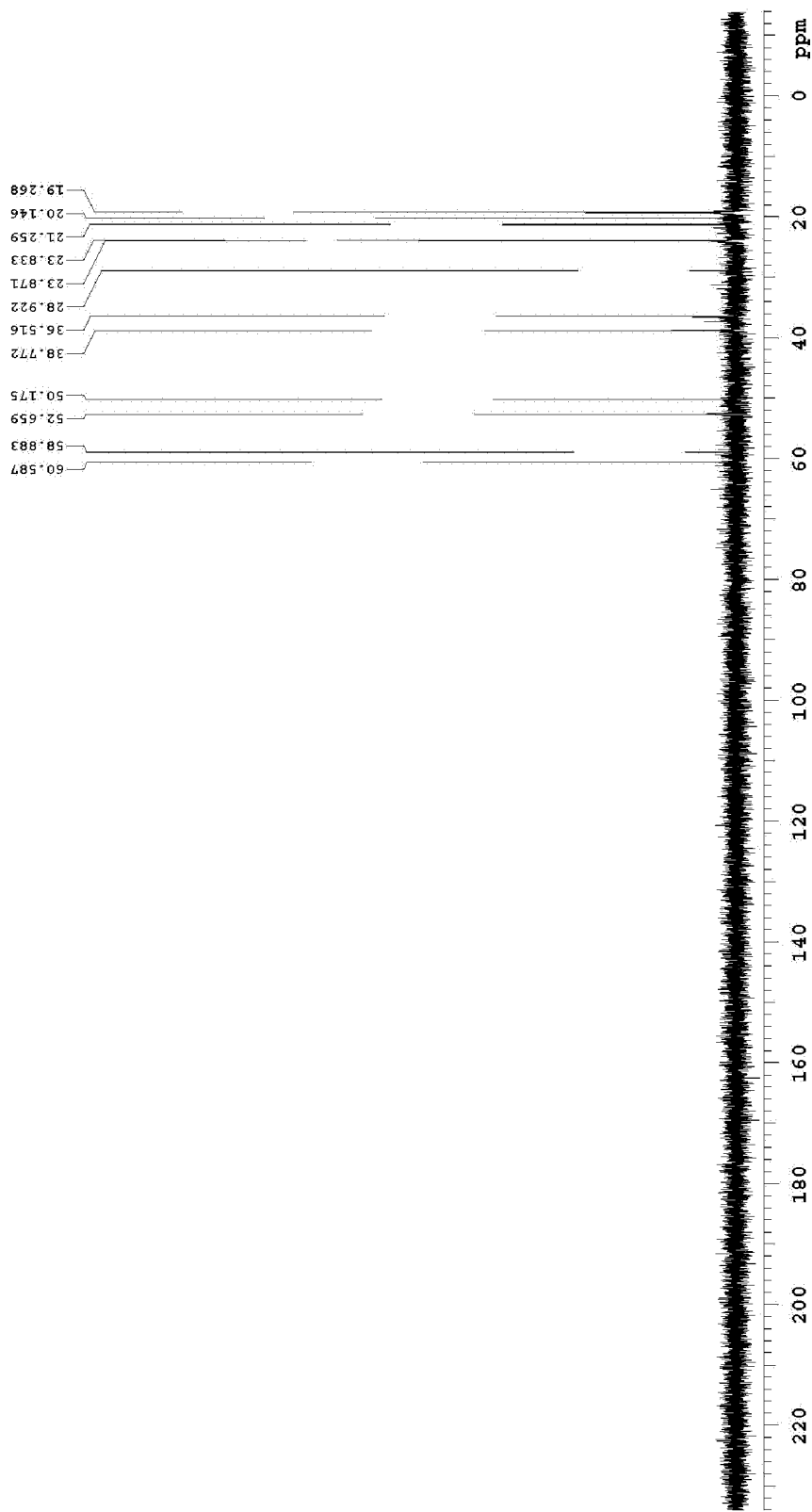
Figure 9:
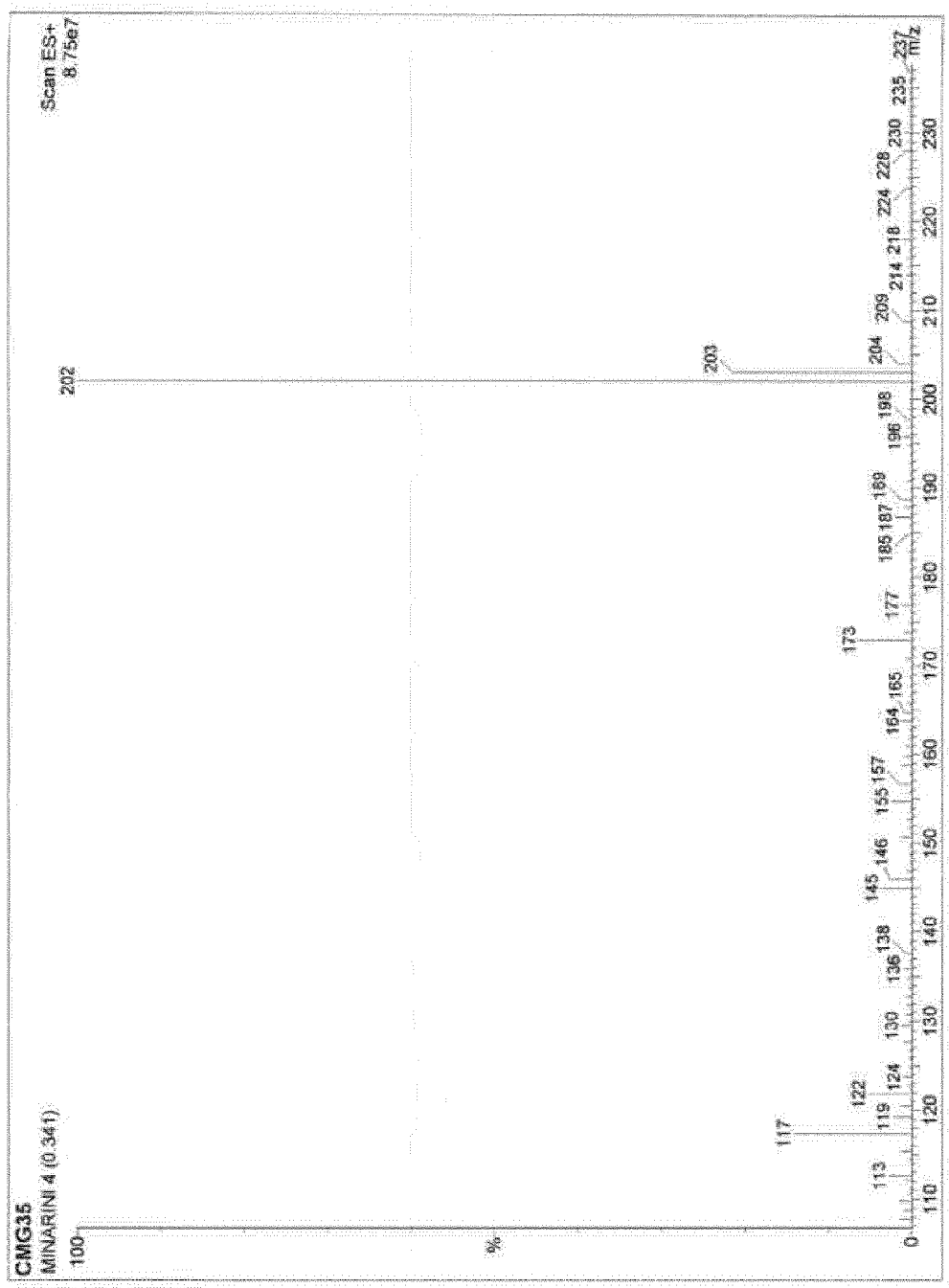

Finally, as stated above, FIGS. 7, 8 and 9 show, respectively, $^1$H-NMR, $^{13}$C-NMR and mass spectra of compound 4, that is, of formula (VI) as defined above.

The stability and reactivity of compounds of formula (I) after exposing a solution thereof to ambient air were also studied.

1. MTT ASSAY

Introduction

MTT Assay is a test used for analysing cell viability (Mosmann, 1983). It is a colorimetric test based on the use of the tetrazolium salt MTT, which measures cell viability which can then be quantified by a microplate spectrophotometric reader. MTT (3-(4,5-dimethylthiazol-2-yl)-2,5-diphenyltetrazolium bromide, a tetrazole), a yellow compound, is reduced to formazan, a purple substance, in cellular mitochondria. The absorbance of this coloured solution can be quantified by measuring it at a given wavelength (570 nm) using a spectrophotometer. The maximum absorbance will depend on the solvent used. This reduction only takes place when the mitochondrial reductase enzymes are active, and the conversion to formazan can therefore be related directly to the number of viable cells. When the amount of formazan produced by cells treated with a substance is compared with the amount produced by untreated control cells, it is possible to deduce the efficacy of the tested substance in causing cell death by producing a dose-response curve. The solutions of MTT solubilised in PBS or cell culture medium, without phenol red, are of a yellowish colour. In viable cells, the mitochondrial dehydrogenases cut the tetrazolium ring, producing purple formazan crystals which are insoluble in aqueous solutions. The crystals can be dissolved in acidified isopropanol or DMSO. The resulting purple solution is analysed by spectrophotometry. An increase in the number of cells will result in an increase in the formazan obtained and in an increase in absorbance. The use of the MTT test has limitations, influenced by: 1) the physiological state of cells and 2) changes in the activity of mitochondrial dehydrogenases in different cell types. Despite this, MTT Assay for cell determination is useful in measuring the cell growth in response to mitogens, antigenic stimuli, growth factors and other reagents that promote cell growth, cytotoxicity studies, and in the creation of cell growth curves.

MTT Assay for cell determination is particularly useful when the cultures are prepared in multi-well plates. For better results, the number of cells should be determined during the exponential growth phase.

Materials
Biological Model

A cell line of NCTC2544 human keratinocytes (Perry V. P. et al., 1957) was obtained from the National Institute for Cancer Research in Genoa, Italy.

| ICLC CATALOG CODE | HL97002 |
|---|---|
| DEPOSITOR | Prof. M. Ferro, DIMES, General Pathology, University of Genoa, Italy |
| BIBLIOGRAFIC REFERENCES | Arch Dermatol Res 1976; 256 (3): 255-260- PMID: 990102<br>Arch Dermatol Res 1976; 261 (1): 27-31 |

Culture Parameters

The cell line was grown in EMEM medium (EBSS) with the addition of 10% FBS, 2 mM L-glutamine, 1% NEAA 1× solution and 1% penicillin (10,000 U/ml)/streptomycin (10,000 µg/ml) mixture, and kept at 37° C., 5% $CO_2$ in 25 cm² culture flasks. Every two days, the confluent cultures were split 1:3-1:6, after washing with PBS 1× (without $Ca^{2+}$ and $Mg^{2+}$), using trypsin/EDTA and seeded at 2-5*10⁴ cell/cm², 37° C., 5% $CO_2$.

Medium for freezing: culture medium with addition of 20% FBS, 2 mM L-glutamine, 1% penicillin/streptomycin mix and 10% DMSO.

Cell quantification: Trypan Blue Assay.
Reagents and Instruments

| REAGENTS | SUPPLIER |
|---|---|
| EMEM (EBSS) without L-glutamine | Lonza (BE12-125F) |
| Liquid NEAA solution (100X) | Lonza (BE13-114E) |
| FBS ES qualified | Lonza (DE14-850F) |
| PEN STREP MIX (Penicillin 10,000 IU/ml, Streptomycin 10,000 IU/ml) | Lonza (DE17-602F) |
| L-glutamine 200 mM | Lonza (BE17-605E) |
| DMSO | Lonza (D2438) |
| PBS 1X without $Ca^{2+}$ or $Mg^{2+}$ | Lonza (BE17-516F) |
| TRYPSIN-VERSENE MIXTURE (EDTA) (1X) | Lonza (BE17-161E) |
| Trypan Blue | Sigma (T8154-20ML) |

| INSTRUMENTS | SUPPLIER |
|---|---|
| Inverted phase contrast microscope (Mod: DMIL) | Leica |
| Laminar flow hood (Mod: Gemini) + UV lamp with anti-glare equipment | Steril Manufacturing Division |
| HeraCell $CO_2$ Incubator (Mod: 150 ADV) | Thermo Scientific |
| Digital 15 l bath for water, from +5° C. to +100° C. (Mod: Swbd1, BS-SWB2D) | Stuart |
| Horizontal freezer −85° C. ULT130, 120 L (Mod: Labfrost, MME-TE21140) | Elcold |
| Bürker chamber for cell count, with terminals (DI-DA-443/3) | Carlo Erba |
| Scales (Mod. AM100) | Mettler |

Methods
Day 1: Seeding the Cells

When the NCTC 2544 human keratinocyte cells had reached a confluence of approximately 80%, they were detached and collected with trypsin/EDTA, seeded at a density of 5×10⁴ cell/ml in 96-well plates, and then incubated at 37° C., 5% $CO_2$ (24 h).

Days 2-3: Exposing Reagents 24-48 h

When the cells had reached a confluence of approximately 80%, they were exposed to increasing concentrations of the aforementioned active compounds according to the invention: N¹-methylspermidine, both as a free base and as trihydrochloride (3HCl) and trimaleate salt; and also N¹-cycloesilspermidine, N¹-ethylspermidine, N¹-propylspermidine, N¹-isobutylspermidine as trihydrochloride (3HCl) salt, and spermidine trihydrochloride salt as a reference for comparison. Each compound was tested in duplicate. The following concentrations of all of the compounds were tested: 1 nM, 500 nM, 1 µM, 500 µM (final concentration in the culture medium). SDS was used as an internal standard.

After preparing the desired dilutions of each compound, the culture medium was removed from the plate and the wells were seeded with 100 µl of each concentration. Controls only containing culture medium were included in each plate.

The cells were incubated at 37° C., 5% $CO_2$, for different treatment times (24-48 h).

Day 4: MTT Assay

At the end of the treatment with the compounds of interest (24-48 h) in a 96-well plate, the medium was removed and replaced with 100 µl/well of MTT solution, and the plates were incubated for 3 h at 37° C., 5% $CO_2$. The MTT salt was dissolved in PBS (5 mg/ml) and added to the cells in a 1:10 dilution in EMEM medium, without phenol red, supplemented with 10% FCS, 2 mM glutamine, 1% NEAA 100× solution (liquid) and 1% antibiotic mix.

The plate was covered with aluminium foil. Subsequently, the medium was carefully removed. 100 µl of DMSO were added to each well to dissolve the purple formazan product. The plates were covered with aluminium foil and stirred for 15 min at room temperature.

The absorbance of the solutions was read at 570 nm with a reference filter at 630 nm in a Biotek ELX808 microplate reader, using a predefined protocol and after correctly defining the layout of the plate.

Data Collection and Statistical Analysis

The optical density data were recorded directly from the software of the Biotek ELX808 microplate reader. The software automatically carries out any transformations.

Transformation 1: calculating the Delta OD 570-630 nm (after automatic white subtraction)

Transformation 2: calculating the % vitality (with respect to the control)

The data obtained were subsequently exported into Excel and statistically and graphically analysed, so as to determine the non-cytotoxic concentrations at which the compounds could be tested.

Reagents and Instruments Used

| REAGENTS | SUPPLIER |
| --- | --- |
| EMEM (EBSS) without L-glutamine | Lonza (BE12-125F) |
| Liquid NEAA solution (100X) | Lonza (BE13-114E) |
| FBS ES qualified | Lonza (DE14-850F) |
| PEN STREP MIX (Penicillin 10,000 IU/ml, streptomycin 10,000 IU/ml) | Lonza (DE17-602F) |
| L-glutamine 200 mM | Lonza (BE17-605E) |
| DMSO | Lonza (D2438) |
| PBS 1X without $Ca^{2+}$ or $Mg^{2+}$ | Lonza (BE17-516F) |
| TRYPSIN-VERSENE (EDTA) Mixture (1X) | Lonza (BE17-161E) |
| Trypan Blue | Sigma (T8154-20ML) |
| MEM Eagle EBSS (2X), WITHOUT L-Gln, phenol red | Lonza (BE12-668-E) |
| MTT | Sigma (M2128 1G) |

| INSTRUMENTS | SUPPLIER |
| --- | --- |
| Inverted phase contrast microscope (Mod: DMIL) | Leica |
| Laminar flow hood (Mod: Gemini) + UV lamp with anti-glare equipment | Steril Manufacturing Division |
| HeraCell $CO_2$ Incubator (Mod: 150 ADV) | Thermo Scientific |
| Digital 15 l bath for water, from +5° C. to +100° C. (Mod: Swbd1, BS-SWB2D) | Stuart |
| Horizontal freezer −85° C. ULT130, 120 L (Mod: Labfrost, MME-TE21140) | Elcold |
| Bürker chamber for cell count, with terminals (DI-DA-443/3) | Carlo Erba |
| Scales (Mod. AM100) | Mettler |
| Microplate reader (Mod: ELX808) + Gen5 Software | BioTek |

Results

Figure 1:
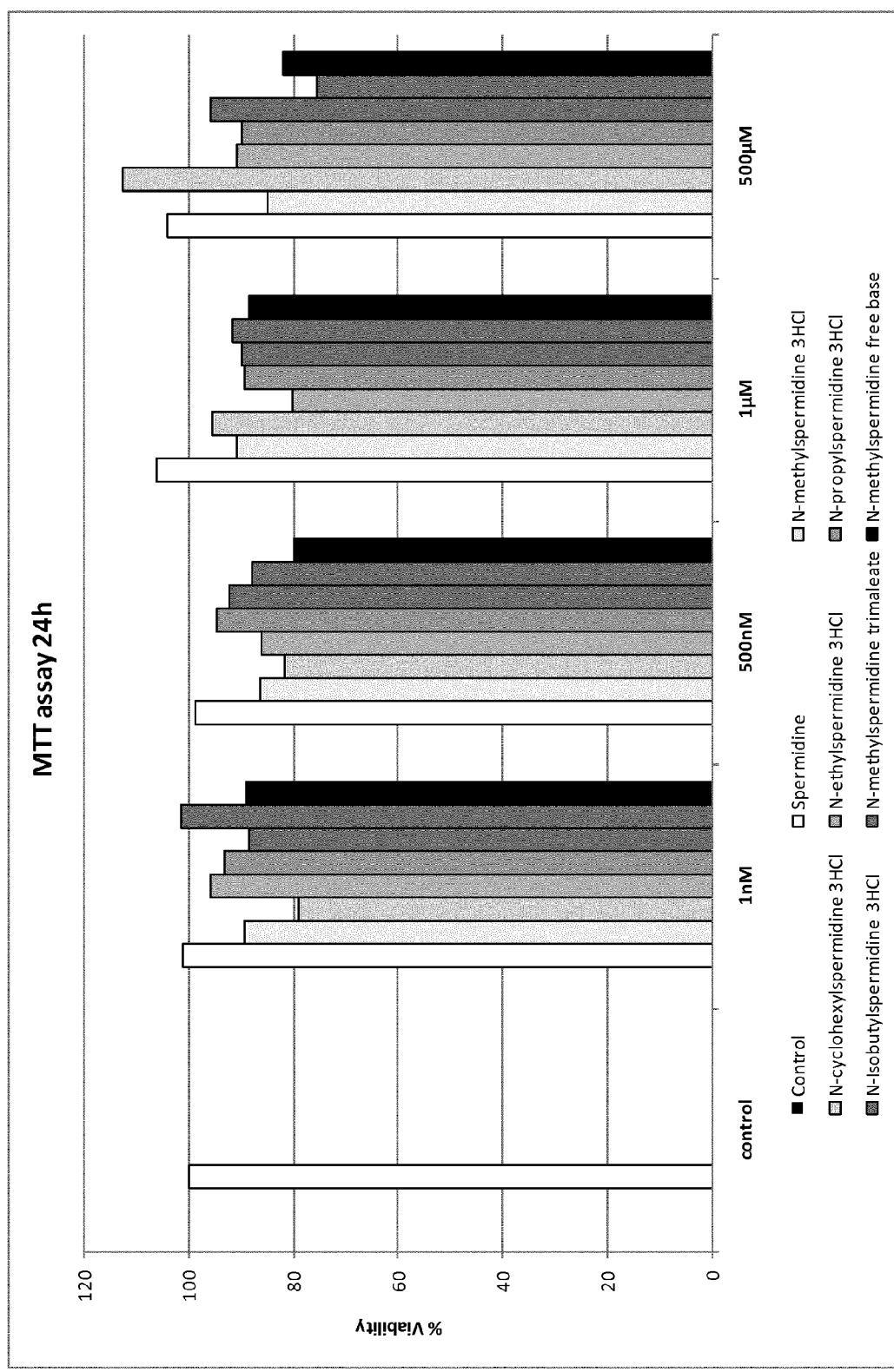
FIGS. 1 and 2 are graphs of the results of an MTT Assay test.
Figure 2:
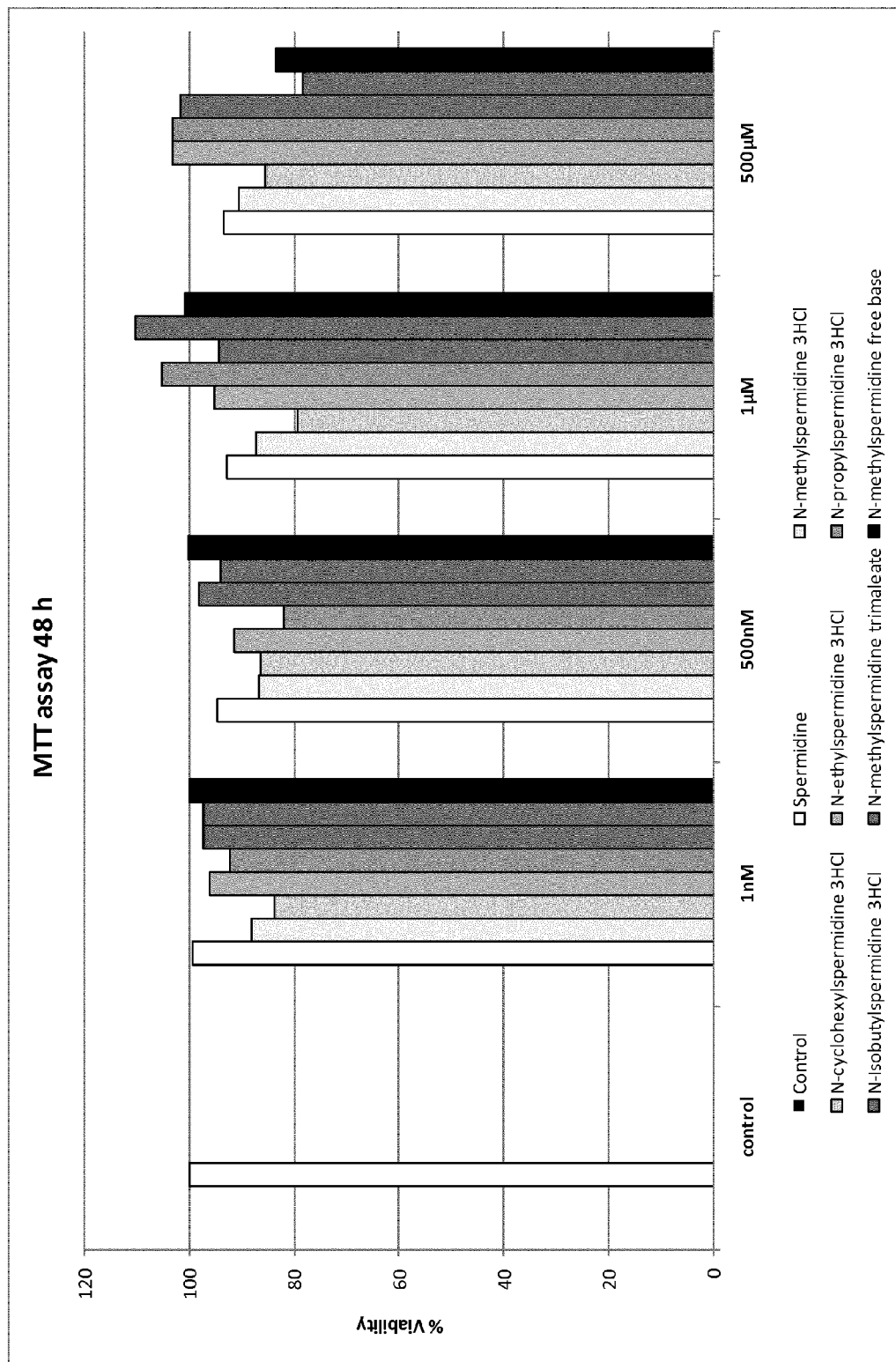

FIGS. 1 and 2 summarise the results obtained in graphs at 24 hours (FIG. 1) and 48 hours (FIG. 2) respectively. The eight columns given there for each group of equal concentration, as specified therein, are to be attributed respectively, from left to right, to: spermidine, $N^1$-methylspermidine, $N^1$-cyclohexylspermidine, $N^1$-ethylspermidine, $N^1$-propylspermidine, $N^1$-isobutylspermidine, all in the form of trihydrochloride salt (3HCl); $N^1$-methylspermidine trimaleate salt; $N^1$-methylspermidine free base.

Cell viability is expressed in percent against the control, that is to say the cell population is grown under standard conditions without the addition of spermidine or of compounds according to the invention. At the concentrations tested (1 nM, 500 nM, 1 mM, 500 mM), spermidine has no cytotoxic effects after 24 or 48 hours of exposing of the cell line of human keratinocytes (NCTC2544). Similarly, the cell viability after treatment for 24 or 48 with the compounds according to the invention (at the same concentrations of spermidine) is not substantially reduced, and in some cases is even improved, demonstrating the lack of cytotoxicity of the compound. The results obtained for the compounds according to the invention are not statistically different from those obtained for spermidine.

In general it may be concluded that MTT assay does not demonstrate cytotoxicity for compounds according to the invention.

2. ANTIOXIDANT TEST

Production of Reactive Oxygen Species (ROS)

The production of reactive oxygen species (ROS) was monitored by spectrofluorometry using 2',7'-dichlorofluorescein diacetate (DCFH-DA) as described by Tobi et al. (Tobi S E, Paul N, T McMillan J. J Photochem. Photobiol, B 2000: 57: 102-112).

The aforementioned NCTC2544 cells (~80% confluence) were detached with trypsin/EDTA and seeded at a density of $5 \times 10^4$ cells per well, in 96-well plates. Subsequently, the cells were treated with the N-methylspermidine according to the invention and spermidine. The following concentrations of N-methylspermidine and spermidine were tested: 1 nM, 500 nM, 1 µM, 500 µM, 1 mM (final concentration in the culture medium).

α-tocopherol (250 µg/ml) was used as a comparison. The plates were incubated at 37° C., in 5% $CO_2$, for 1.5 h. The cells grown on basal medium with 10% FBS were used as a control.

Figure 3:
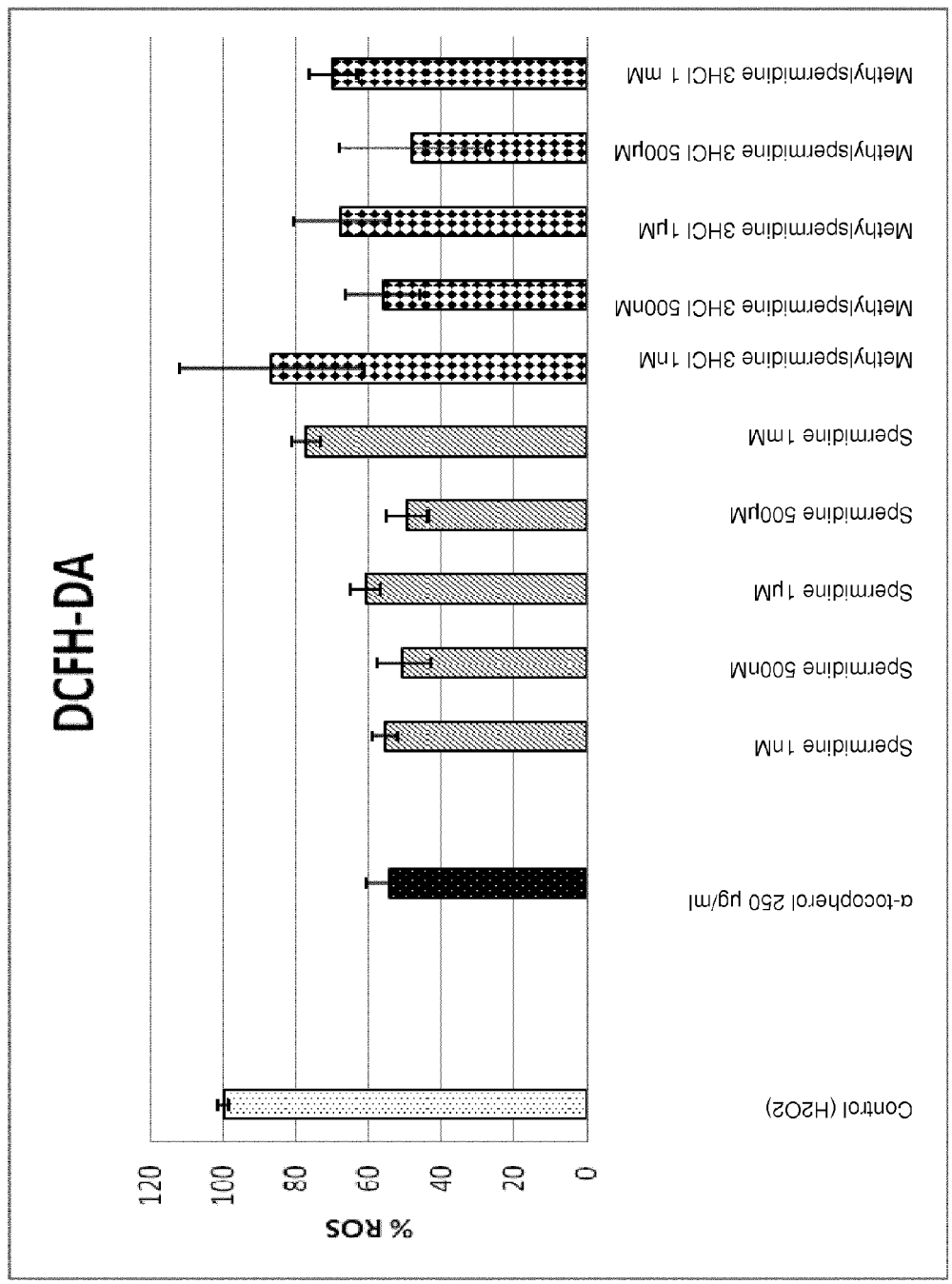
FIG. 3 is a graph of the results of an antioxidant test.

The graph of FIG. 3 summarises the results obtained. The results obtained from determining the intracellular concentration of reactive oxygen species (ROS) confirmed antioxidant activity of spermidine as reported in the literature. Compared to control cells treated with $H_2O_2$, the cells treated with 250 µg/ml of α-tocopherol, spermidine and N-methylspermidine show a decrease in the concentration of ROS products. When comparing the antioxidant activity of spermidine with that of N-methylspermidine, no significant difference was demonstrated.

3. HAIR SHAFT ELONGATION TEST

The activity of N-methylspermidine was tested in an ex vivo model which made it possible to measure the effect on the elongation of the hair shaft.

Materials and Methods

The organ culture of hair follicles (HF) in anagen VI phase involved microdissection of HF from the skin of the human scalp (temporo-frontal area) after informed consent from the subjects who were undergoing surgery (face lifts), in accordance with the Helsinki Declaration and with the approval of the Ethics Committee of the University of Lübeck. In this model, the growth phase (anagen) of HF continued for several days to produce a pigmented shaft at a speed similar to the anagen phase in vivo, additionally exhibiting a cyclical growth activity in vitro, spontaneously entering the regression phase of the cycle hair (catagen).

For immunohistochemical studies, the isolated follicles were cultured for 6 consecutive days.

Spermidine, N-methylspermidine and the vehicle (distilled water) were administered once for each change of culture medium (every 48 hours), at a concentration of 0.5 µM.

The frozen sections were stored at −80° C. until they were used.

Hair Growth Measurement

The measurements of the shaft elongation after the treatment with vehicle, spermidine and N-methylspermidine were taken on days 0, 1, 4 and 6, using a Zeiss inverted binocular microscope with one eyepiece containing a reticle (Carl Zeiss, Oberkochen, Germany).

Results

Figure 4:
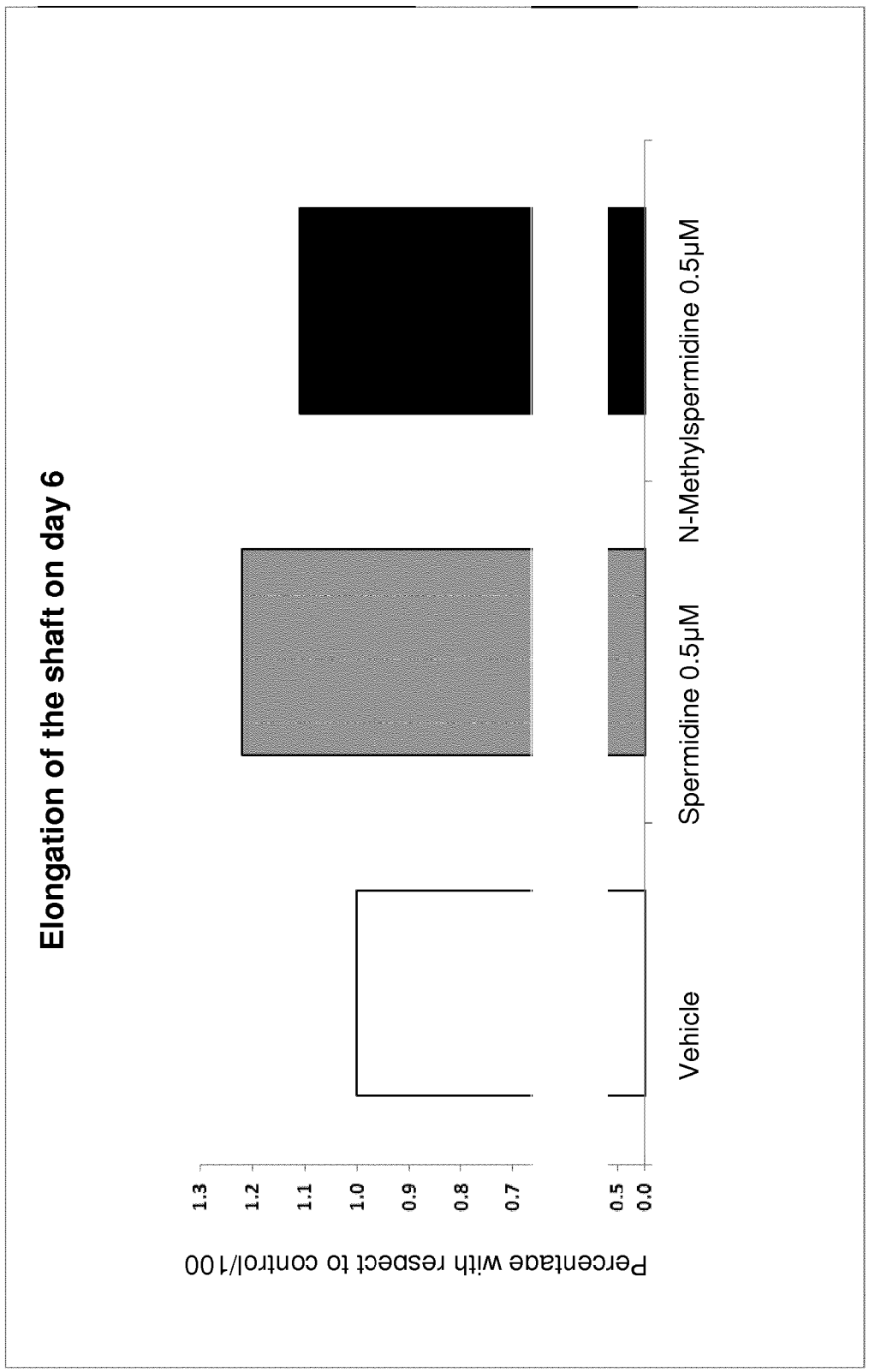
FIG. 4 is a graph of the results of a hair elongation test.

The results of the shaft elongation are shown in the graph of FIG. 4, which shows the results on day 6. Both spermidine and N-methylspermidine according to the invention improve the elongation of the hair shaft significantly with respect to the vehicle. The observed difference between spermidine and N-methylspermidine is not statistically significant, and therefore the elongation effect should be considered comparable in the two cases under comparison.

4. RESULTS FOR THE ANAGEN AND CATAGEN PHASES

Figure 5:
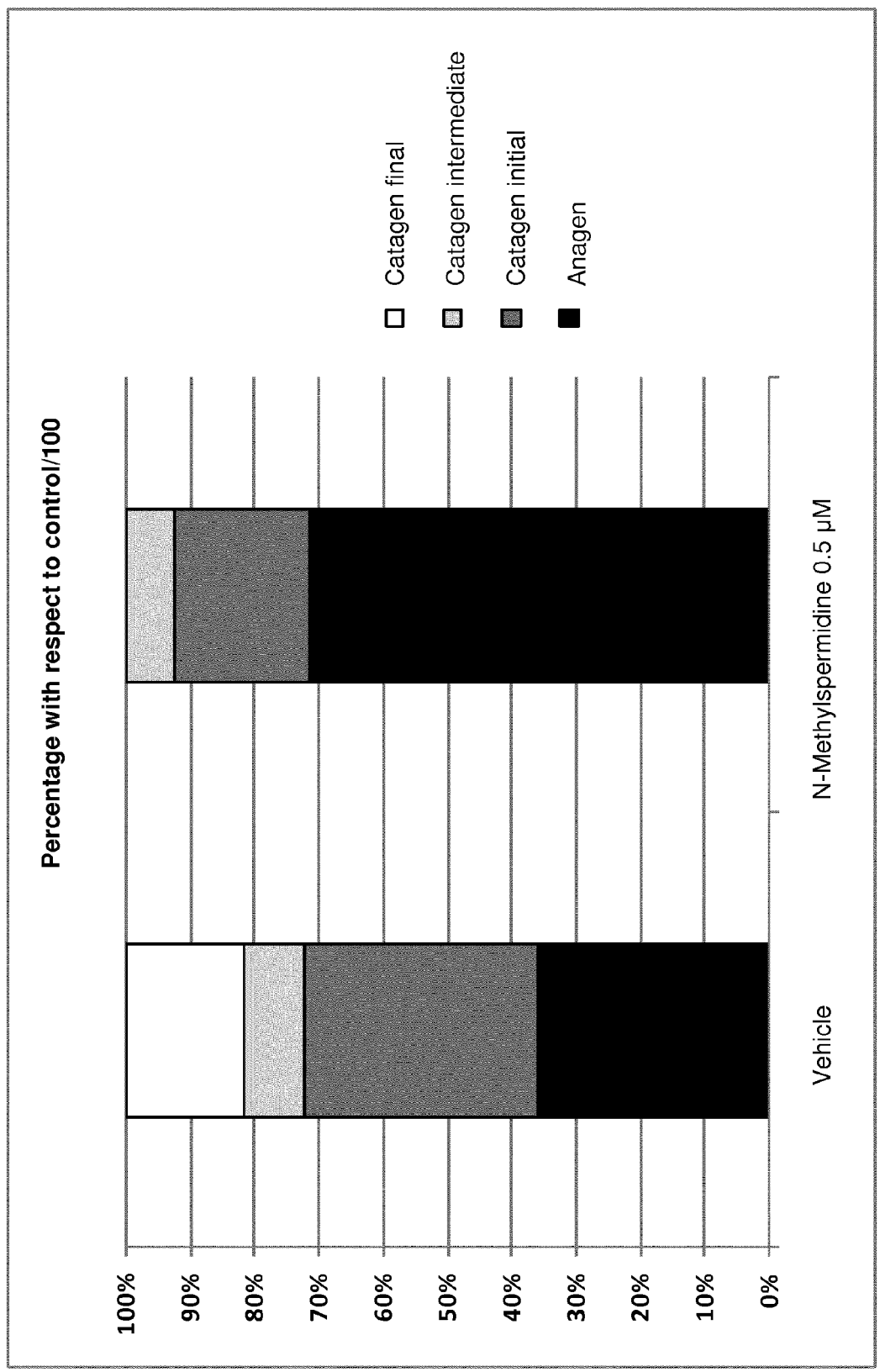
FIGS. 5 and 6 are graphs of the results for the anagen and catagen phases in the test of FIG. 4.
Figure 6:
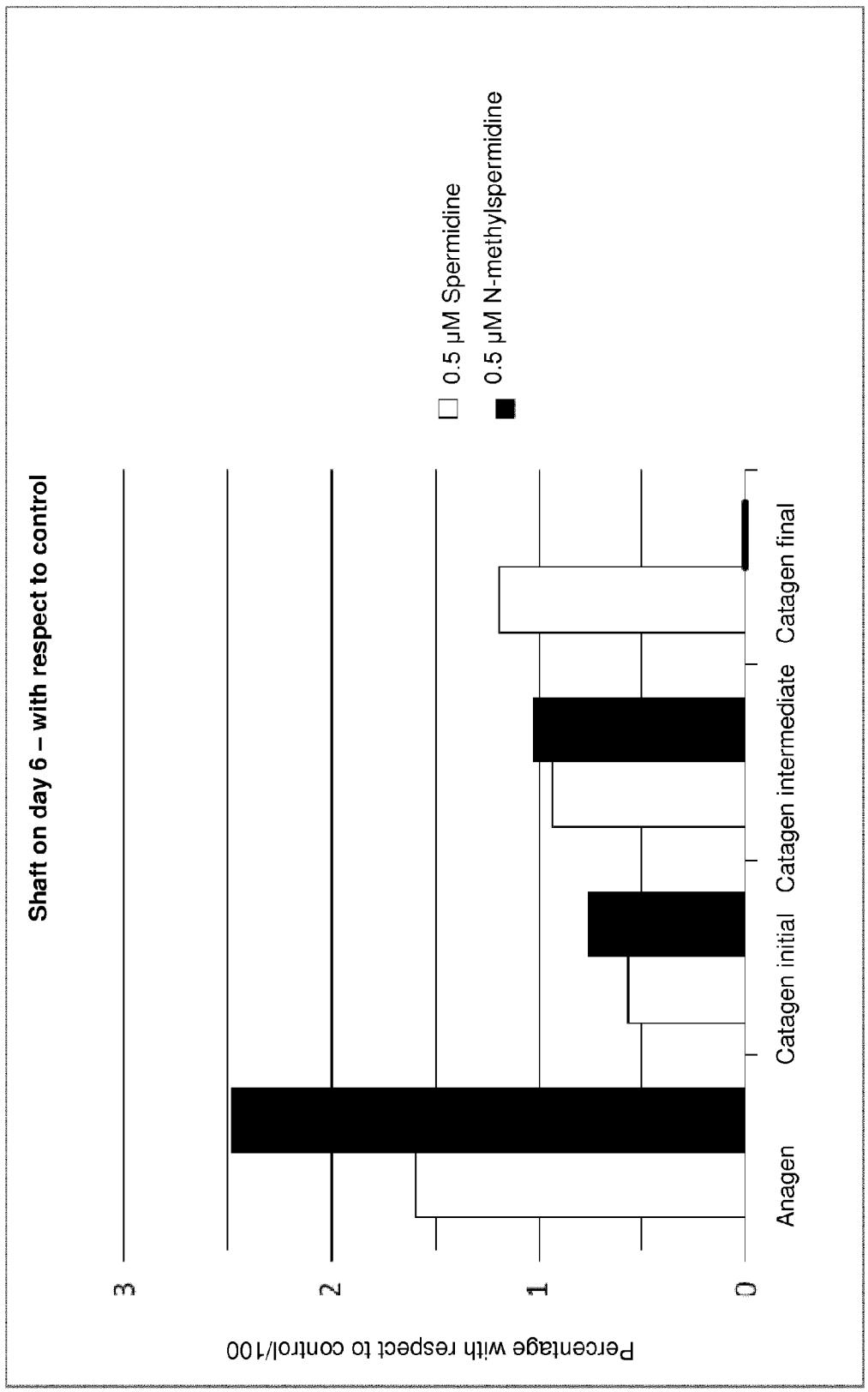

The following results for the anagen and catagen phases, summarised in the graphs of FIGS. 5 and 6, were also obtained from the same ex vivo model of hair follicles (HF) described for the previous test of elongation of the hair shaft.

The graph of FIG. 5 shows the percentage of follicles treated with N-methylspermidine in the different phases of the growth cycle.

From this, it can be seen that after 6 days of treatment N-methylspermidine brings about a significant increase in the percentage of hair follicles in the anagen phase and a decrease in those in catagen. In the presence of N-methylspermidine, only 30% (approximately) of follicles enter catagen spontaneously, whilst in the presence of the vehicle more than 60% of the follicles enter catagen.

The graph of FIG. 6 shows the corresponding percentage values for the control of the phases of the follicle obtained for spermidine (0.5 µM) and N-methylspermidine (0.5 µM).

The comparison between the two compounds surprisingly demonstrates a greater effect of prolonging the anagen phase in the case of N-methylspermidine than with spermidine. Therefore, the number of hairs entering the catagen phase (divided into stages: initial, intermediate and final) was significantly lower after treatment with N-methylspermidine than with spermidine.

5. RESULTS FOR THE REACTIVITY

The properties of 1,4-butanediamine,N-(3-aminopropyl)-$N^1$-methyl (II) and 1,4-butanediamine,N-(3-aminopropyl)-$N^1$-cyclohexyl (III) after exposure to air were studied by comparison with the corresponding non-substituted derivative, in which the $N^1$ amine group lacking the R substituent becomes a secondary amine group, namely 1,4-butanediamine,N-(3-aminopropyl). Since one of the common products of oxidation of the secondary amino group takes the form of the N-nitroso derivatives which are formed by reaction with the nitrogen oxides present in the air, the nitrosated derivatives which were formed upon leaving a solution of the test compounds in contact with the ambient air were determined as a parameter of reactivity.

Materials and Methods

The instrumentation used consisted of a stage on which both the analysis of the nitrite ions and the analysis of the N-nitrosamines were carried out, the latter under strong denitrosating conditions. The nitrogen oxide which developed in accordance with the amount of nitrite ions and that which developed in accordance with the quantity of nitroso groups were evaluated by way of a chemiluminometric detector.

The content of $NO^{2-}$ ions was analysed using a reducing mixture of acetic acid/potassium iodide (5 ml/1 ml of 5% $H_2O$ soln.) at a temperature of 0-4° C. The nitroso groups were analysed using a denitrosating mixture of acetic acid/hydrobromic acid (5 ml/1 ml) at a temperature of 70° C.

The reagents are commercially available for example from Sigma-Aldrich. High-purity gases ($He_2$ and NO) were used.

The method for determining air oxidation of the compound was as follows.

a) a 2 mM solution of the test substance in purified water was doubly seeded, at an amount equal to 500 µl in appropriate wells of six-well plates of inert plastics material (polystyrene);

b) the solution in each well was diluted with 500 µl of a mixture of purified water and ethanol (85/15) free from contamination. This promotes the dispersion of the liquid film on the surface of the well;

c) the plate prepared in this manner is exposed to ambient air for 72 h d) at the end of the exposure time, the residue in the well is eluted with 1 ml of purified water and then used for the chemiluminometric analysis.

Results

| Compound | Nitroso derivatives after 72 h exposure |
| --- | --- |
| 1,4-butanediamine,N-(3-aminopropyl) | 2.3 ppm |
| 1,4-butanediamine,N-(3-aminopropyl)-$N^1$-methyl | absent |
| 1,4-butanediamine,N-(3-aminopropyl)-$N^1$-cyclohexyl | absent |

6. CONCLUSIONS

In terms of the lack of cytotoxicity, antioxidant activity towards ROS and elongation of the shaft, the above experiment demonstrates that a compound according to the invention provides results not substantially different from those obtainable with spermidine.

Also, surprisingly, N-methylspermidine appears to have a higher activity than spermidine in prolonging the anagen phase of the hair.

Although stimulating elongation of the shaft and prolonging anagen both contribute to physiological growth of the hair, from the clinical point of view the result for the extension of the anagen phase may be considered more significant and relevant as regards the action of elongating the hair shaft, since a protracted anagen phase has a direct positive influence on the reduction of hair loss, which is the main object of the invention.

An activity of prolonging the anagen phase and relative inhibition of the catagen phase, as indicated above for N-methylspermidine, is useful in combating many different forms of hair loss, or alopecia, characterised by an excessive effluvium due to a non-physiological reduction in the anagen phase, for example resulting from of androgens, perifollicular inflammation, iron deficiency and estrogens, or the administration of drugs which cause non-physiological effluvium as a side effect.

From the above description as a whole, it can therefore be seen that the compounds of general formula (I) are active in accordance with the objects of the present invention, and also sufficiently stable to allow effective application for topical use on the scalp without potentially being transformed into a different substance, which is no longer active, as a result of oxidation.

The invention claimed is:

1. A method for treating hair loss in a human subject comprising:
administering one or more compounds selected from $$H_2N-(CH_2)_3-N^1(CH_3)-(CH_2)_4-NH_2; \quad (II)$$

$$H_2N-(CH_2)_3-N^1(C_6H_{11})-(CH_2)_4-NH_2; \quad (III)$$

$$H_2N-(CH_2)_3-N^1(C_2H_5)-(CH_2)_4-NH_2; \quad (IV)$$

$$H_2N-(CH_2)_3-N^1(C_3H_7)-(CH_2)_4-NH_2; \quad (V)$$

$$H_2N-(CH_2)_3-N^1(C_4H_9)-(CH_2)_4-NH_2; \quad (VI)$$

and pharmaceutically acceptable salts thereof.

2. Method according to claim 1, wherein said one or more compound is applied topically to the scalp.

3. Method according to claim 1, wherein said one or more compound is $N^1$-methylspermidine, or N-(3-aminopropyl)-$N^1$-methyl-1,4-butanediamine of formula:

$$H_2N-(CH_2)_3-N^1(CH_3)-(CH_2)_4-NH_2. \quad (II)$$

4. Method according to claim 1, wherein said one or more compound is $N^1$-cyclohexylspermidine, or N-(3-aminopropyl)-$N^1$-cyclohexyl-1,4-butanediamine of formula:

$$H_2N-(CH_2)_3-N^1(C_6H_{11})-(CH_2)_4-NH_2. \quad (III)$$

5. Method according to claim 1, wherein said one or more compound is $N^1$-ethylspermidine, or N-(3-aminopropyl)-N1-ethyl-1,4-butanediamine of formula:

$$H_2N-(CH_2)_3-N^1(C_2H_5)-(CH_2)_4-NH_2. \quad (IV)$$

6. Method according to claim 1, wherein said one or more compound is $N^1$-propylspermidine, or N-(3-aminopropyl)-$N^1$-propyl-1,4-butanediamine of formula:

$$H_2N-(CH_2)_3-N^1(C_3H_7)-(CH_2)_4-NH_2. \quad (V)$$

7. Method according to claim 1, wherein said one or more compound is $N^1$-isobutylspermidine, or N-(3-aminopropyl)-$N^1$-isobutyl-1,4-butanediamine of formula:

$$H_2N-(CH_2)_3-N^1(C_4H_9)-(CH_2)_4-NH_2. \quad (VI)$$

8. Method according to claim 1, wherein said one or more compound is in the form of trihydrochloride salt.

9. Method according to claim 1, wherein said one or more compound is in the form of salt with maleic acid.

10. Method according to claim 1, wherein said administering promotes physiological growth of the hair by simultaneously stimulating elongation of the hair shaft and prolonging the anagen phase.

* * * * *